United States Patent
Lust et al.

(10) Patent No.: US 8,430,853 B2
(45) Date of Patent: Apr. 30, 2013

(54) IMPLANTATION INSTRUMENTS, SYSTEM, AND KIT FOR PUNCTAL IMPLANTS

(75) Inventors: Victor Lust, Jacksonville, FL (US); Oscar P. L. Boel, Tilburg (NL); Hassan Chaouk, Jacksonville, FL (US); Brian Schwam, Jacksonville, FL (US); Stephen R. Beaton, Jacksonville, FL (US); Vincent G. McAteer, Jacksonville, FL (US)

(73) Assignee: Johnson & Johnson Vision Care, Inc., Jacksonville, FL (US)

(*) Notice: Subject to any disclaimer, the term of this patent is extended or adjusted under 35 U.S.C. 154(b) by 639 days.

(21) Appl. No.: 12/701,271

(22) Filed: Feb. 5, 2010

(65) Prior Publication Data

US 2011/0196317 A1   Aug. 11, 2011

(51) Int. Cl.
*A61M 35/00* (2006.01)
*A61M 29/00* (2006.01)

(52) U.S. Cl.
USPC .............................. 604/294; 606/191; 604/521

(58) Field of Classification Search .................. 604/294, 604/521; 606/191
See application file for complete search history.

(56) References Cited

U.S. PATENT DOCUMENTS

| | | | |
|---|---|---|---|
| 5,335,871 A | 8/1994 | Fissmann et al. | |
| 5,643,280 A | 7/1997 | Del Rio et al. | |
| 5,741,292 A | 4/1998 | Mendius | |
| 6,344,047 B1 | 2/2002 | Price et al. | |
| 6,527,780 B1 | 3/2003 | Wallace et al. | |
| 2004/0068286 A1* | 4/2004 | Mendius | 606/191 |
| 2005/0154399 A1 | 7/2005 | Weber | |
| 2007/0027452 A1 | 2/2007 | Varner et al. | |
| 2007/0299516 A1 | 12/2007 | Cui et al. | |
| 2009/0036842 A1 | 2/2009 | Pinedjian | |
| 2009/0105749 A1 | 4/2009 | de Juan et al. | |
| 2010/0057024 A1 | 3/2010 | Bernard | |
| 2010/0255061 A1 | 10/2010 | de Juan, Jr. et al. | |
| 2011/0196317 A1 | 8/2011 | Lust | |

FOREIGN PATENT DOCUMENTS

WO   WO 2004/034518 A2   4/2004

OTHER PUBLICATIONS

PCT International Search Report for PCT US2011/0328884 Date of Mailing Mar. 5 2012.
International Search Report dated May 9 2012 from International Application No. PCT/US/2011/032884.

* cited by examiner

*Primary Examiner* — Melanie Hand

(57) ABSTRACT

Described and illustrated are various insertion instruments, cap, plug, method and kit. In one aspect, a cap for a punctal insertion instrument is shown and described. In a further aspect, a punctum plug insertion system that includes the instrument and the cap is provided. In yet a further aspect, a method of releasing a punctum plug from a plug holder is provided. Additionally, a kit that contains the plug insertion instrument, cap, plugs, and instructions for use is provided.

10 Claims, 8 Drawing Sheets

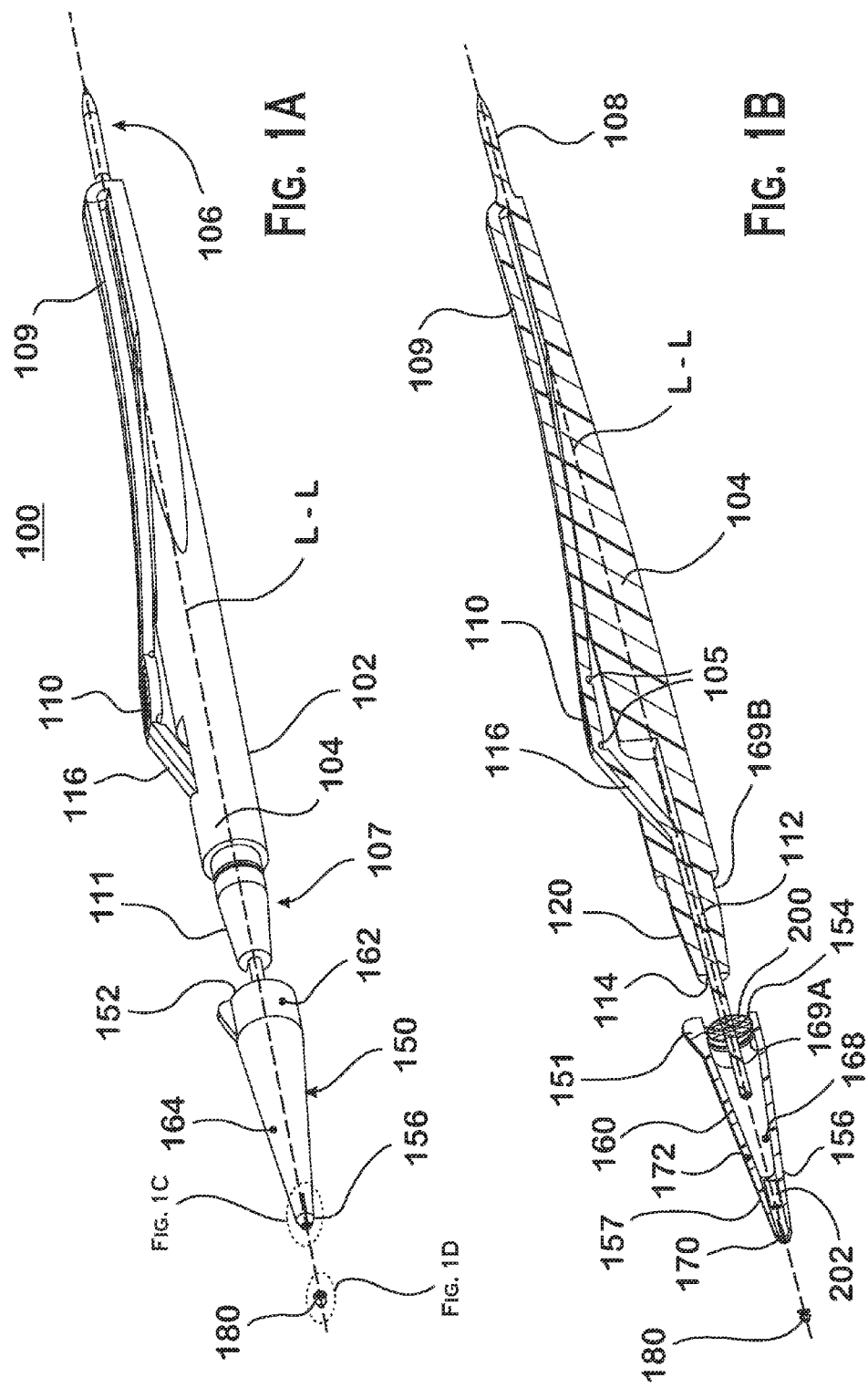

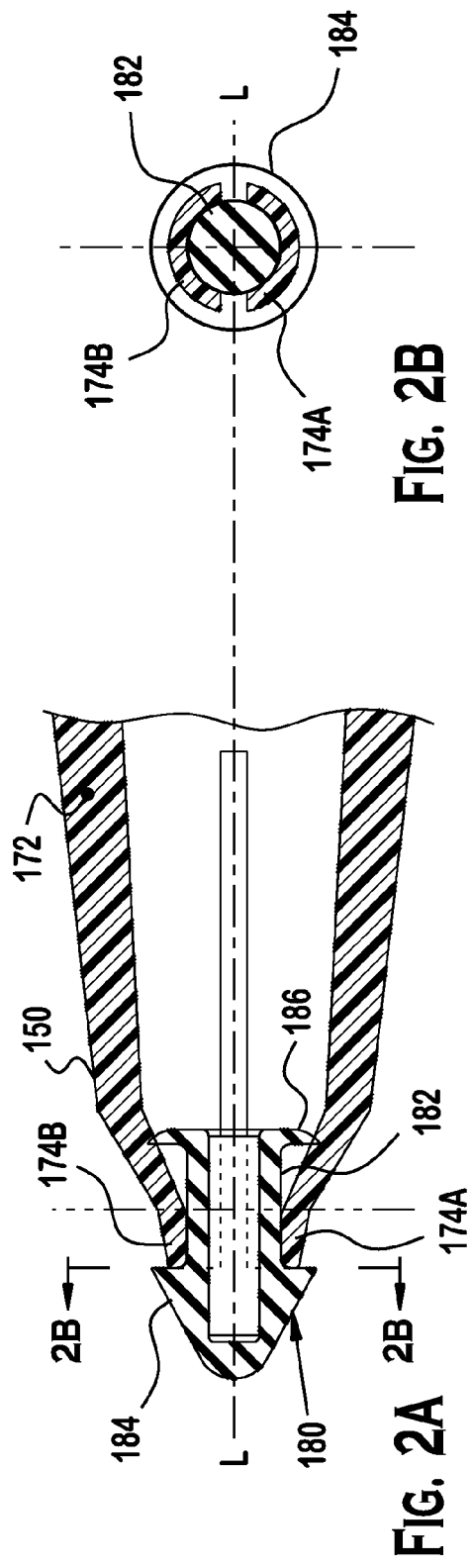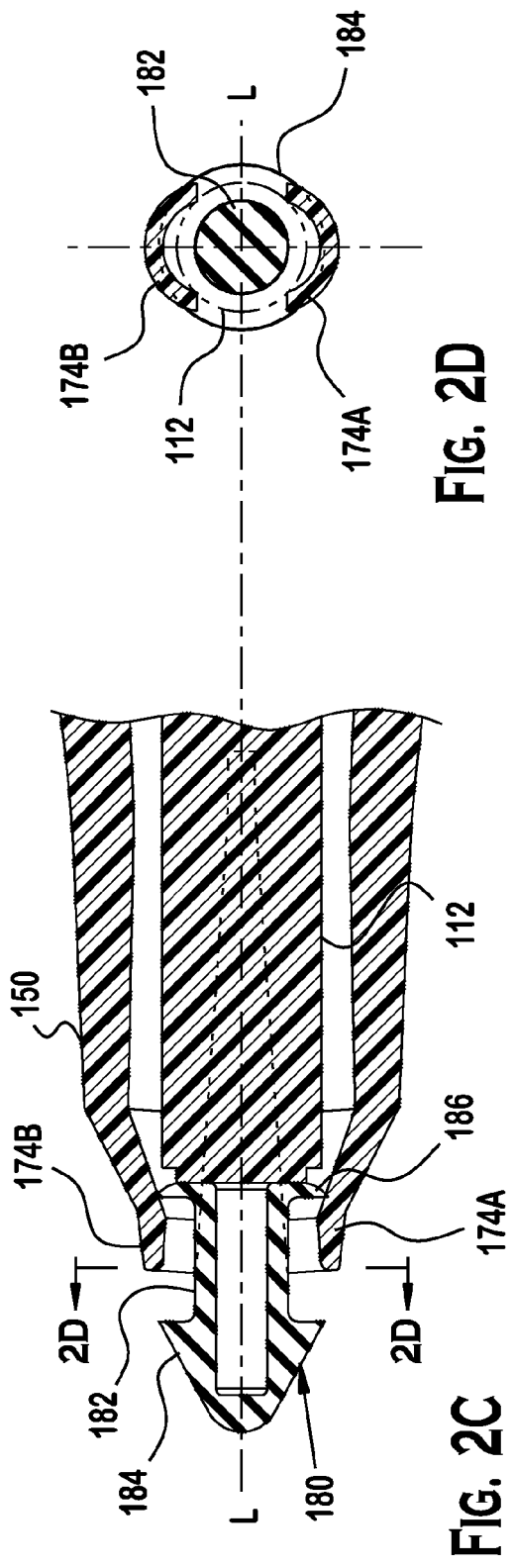

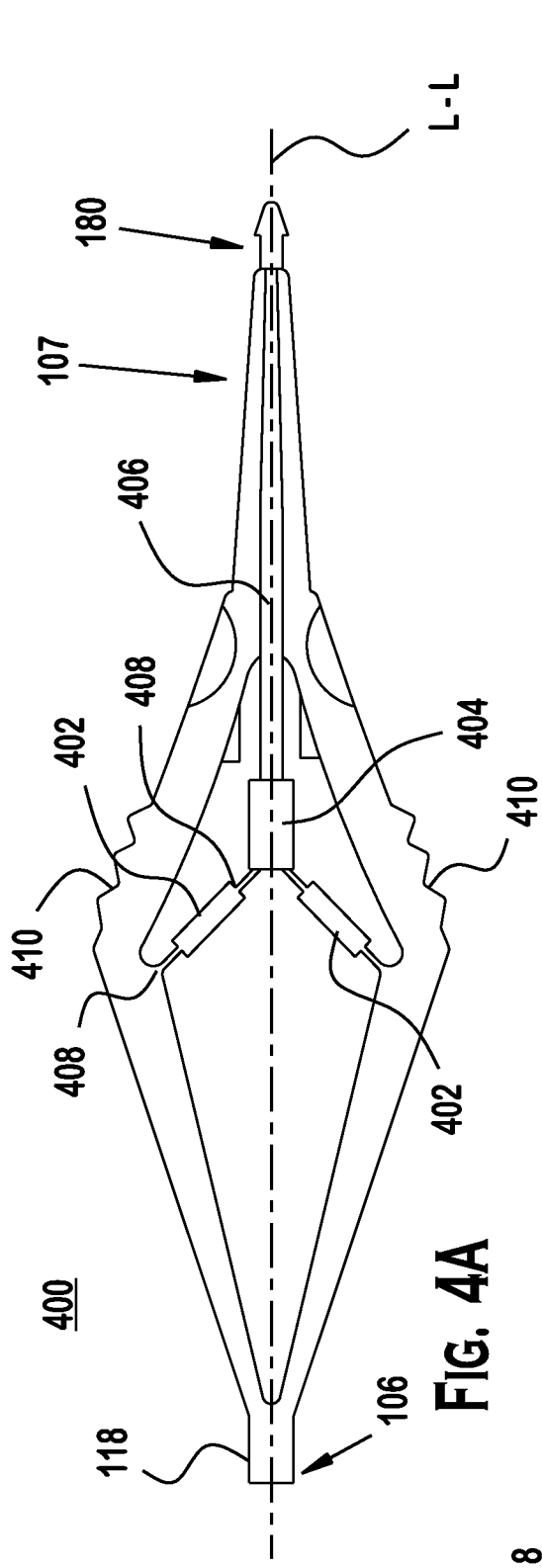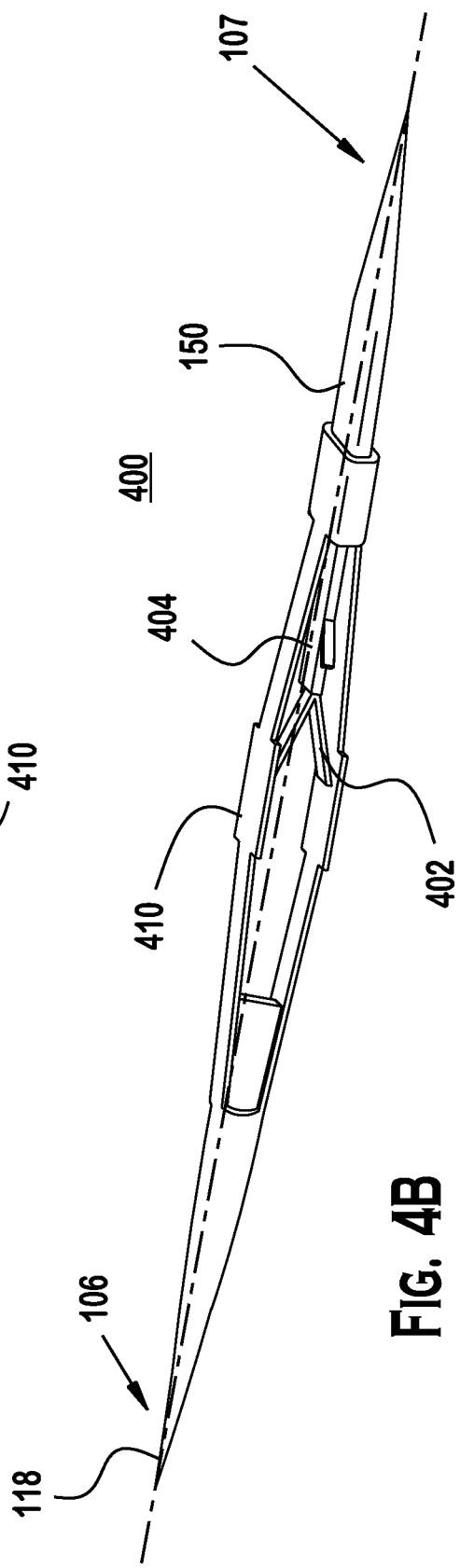

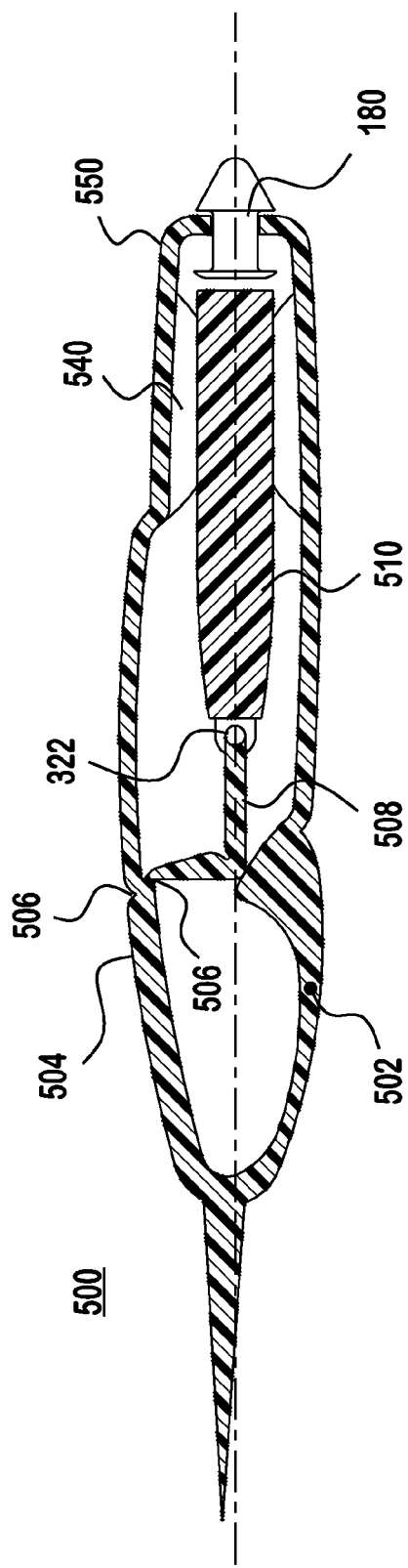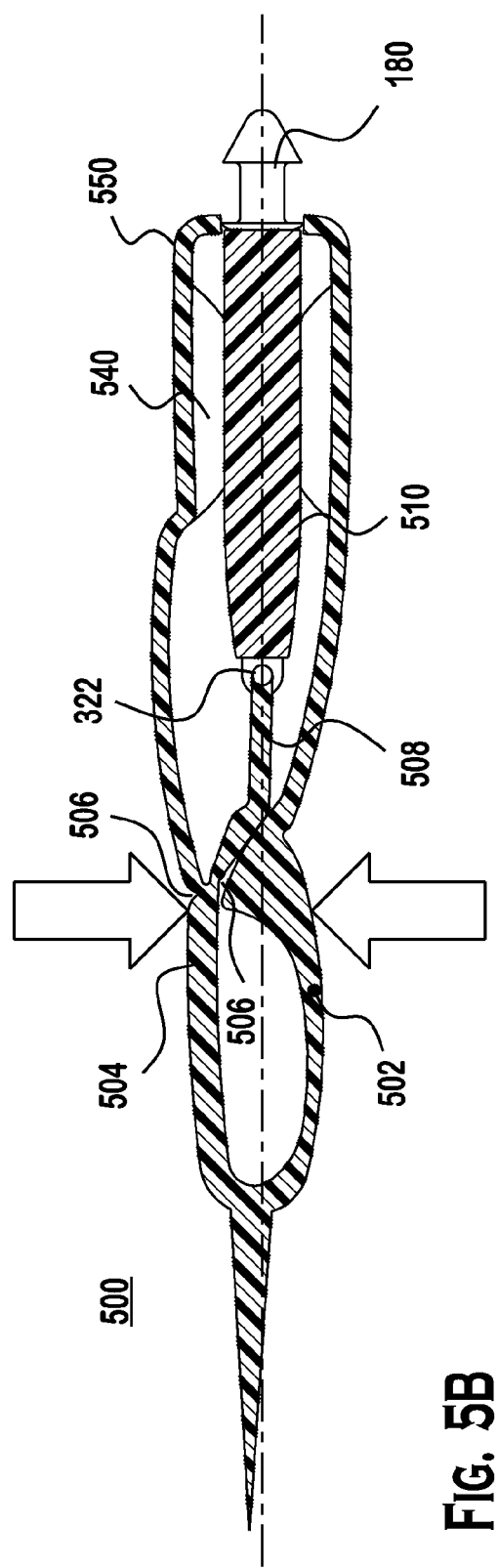
FIG. 5A
FIG. 5B

IMPLANTATION INSTRUMENTS, SYSTEM, AND KIT FOR PUNCTAL IMPLANTS

BACKGROUND

One of the most common problems treated by eye physicians is dry eye syndrome. It is believed that over ten million Americans suffer from this condition, which is usually caused by problems relating to the tear film that lubricates the eyes. Tears are formed in several glands around the eye. The water layer is produced in the lacrimal gland under the upper eyelid. Other glands in the lids make the oil and mucus layers. Blinking spreads the tears over the eye. Excess tears drain into ducts in the corner of the eye by the nose.

Problems with the tear film may occur due to the aging process. For example, a person produces less oil (up to 60% less) in the tear film at age 65 as compared to at age 18. The reduction of oil in the tear film may allow water in the film to evaporate faster, which leaves the cornea dry.

The use of plugs to block or reduce drainage into the tear ducts can be an effective step in treating moderate to severe dry eye that is incompatible with artificial tear drops and ointments. By blocking this outflow with a plug, called punctal or punctum plug, the tears tend to remain over the eye for a longer time. Punctal plugs have demonstrated to increase the comfort level and lower the frequency of artificial tear use in most dry eye patients.

The known punctum plugs are typically configured in the form of a cylindrical body with a blind hole extending from one end of the plug to allow the plug to be mounted over an insertion rod of an insertion tool, which is shown, for example, by U.S. Pat. Nos. 5,741,292; 5,643,280; 6,344,047; 6,527,780; and 5,335,871. Upon insertion of the plug into the tear ducts, the insertion rod is used to release the plug from the tool.

While the plugs can be used as a technique to control outflow of tears, active agents are frequently administered at the same time to the eye for the treatment of ocular diseases and disorders. Several examples of punctum plug are shown and described in U.S. Patent Publication No. 20070299516, which are hereby incorporated by reference herein to this application. In at least one example of such plug, an active agent is loaded into the blind bore of such plug.

SUMMARY OF THE DISCLOSURE

Utilizing the active agents with the punctum plug for greater efficacy in the treatment of dry eye syndromes and other related disorders of the eyes requires an effective insertion tool and those presently available are difficult to use or have performance limitations.

Accordingly, one aspect of the invention is an insertion instrument for implanting punctum plugs that lack a blind bore, including those plugs loaded with one or more active agents in a location where a blind bore would normally be formed.

In another aspect, an insertion instrument is provided. In another aspect, a cap for a punctal insertion instrument is shown and described. In a further aspect, punctum plug insertion system that includes the instrument and the cap is provided.

In yet a further aspect, a method of releasing a punctum plug from a plug holder is provided.

Additionally, a kit that contains the plug insertion instrument, cap, plugs, and instructions for use is provided.

BRIEF DESCRIPTION OF THE DRAWINGS

FIG. 1A illustrates a perspective view of an exemplary embodiment of a punctum plug insertion system having a punctum plug, punctum cap, and insertion instrument.

FIG. 1B illustrates a sectional perspective view of the exemplary system of FIG. 1A.

FIG. 2A illustrates in a plan view of a variation of the instrument of FIG. 1A whereby the plug illustrates mounted to the cap and unreleased from the instrument.

FIG. 2B illustrates a sectioned view of the components as viewed from sectional line 2B-2B.

FIG. 2C illustrates a plan view during a plug release sequence of the embodiment of FIG. 2B.

FIG. 2D illustrates a sectioned view of the components as viewed from sectional line 2C-2C.

FIG. 4A illustrates a plan view of yet another variation of the embodiment of FIGS. 3A and 3B.

FIG. 4B illustrates a perspective view of the embodiment of FIG. 4A.

FIGS. 5A and 5B illustrate respective sectional side views of yet a further embodiment of an insertion instrument.

DETAILED DESCRIPTION OF ILLUSTRATIVE EMBODIMENTS

Figure 1C:
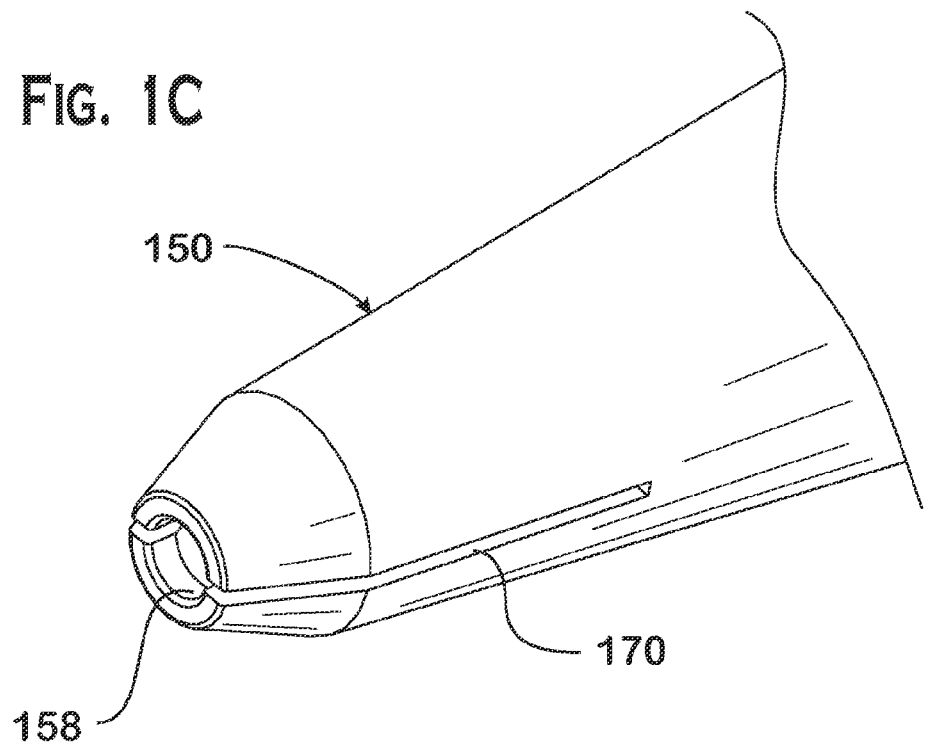
FIG. 1C illustrates a close-up perspective view of a distal portion of the insertion instrument of FIG. 1A.

The detailed description illustrates by way of example, not by way of limitation, the principles of the invention. As used herein, the term "punctal plug" refers to a device of a size and shape suitable for insertion into the inferior or superior lacrimal canaliculus of the eye through the inferior or superior lacrimal punctum. Additionally, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Portions of the disclosure of this document contain material that is subject to copyright protection. The copyright owner reserves all copyright rights to these portions including, without limitation the instructions for use described herein.

Referring to FIG. 1A, a system 100 to deliver or insert a punctum plug 180 is shown in perspective view along a longitudinal axis L-L. The system 100 includes an insertion tool or instrument 102 that includes instrument body 104. The instrument body 104 extends from a proximal end 106 (i.e., the end nearest an operator holding the instrument 102 for its intended use) to a distal end 107 (i.e., the end furthest away from an operator holding the instrument 102 for its intended use) along the longitudinal axis L-L. The instrument 102 has an actuator 110 disposed near the distal end 107. The actuator 110, in the form of a button, may be connected to an actuation member 112, which is configured to move along the longitudinal axis L-L through a body opening 114 provided in the instrument body. The actuation member 112 may be formed of any configuration as long as such configuration allows the actuation member 112 to reciprocate along the longitudinal axis L-L in the body opening 114. Preferably, the actuation member 112 is configured as a generally cylindrical rod. The actuation member 112 is connected to the actuator 110 via an arm 116 that is angled with respect to the longitudinal axis L-L. The arm 116 is coupled to the actuator 110 via at least one suitable hinge 105, such as, for example, an unbiased hinge, spring-biased hinge or preferably a living hinge 105.

Although the embodiment shown in FIG. 1A is provided with one hinge, other embodiments may be provided with two or more hinges, as shown in FIGS. 3A, 3B, 4A, and 4B. At the proximal end 106 of such embodiments, a dilation member 108 can be provided to assist in the dilation of the tear ducts prior to insertion or implantation of the punctum plug 180. The dilation member 108 may be a conical taper with diameters ranging from about 1.5 mm to about 0.1 mm. The shaft attached to the dilation member 108 is generally cylindrical shaft with a diameter of about 0.1 cm to about 0.8 cm with a length of about 10 mm to about 100 mm. The dilation member 108 may be connected to the actuator 110 via a cantilever member 109, which provides a suitable bias for the actuator 110 to remain in the unreleased or non-actuated position. The stiffness modulus of the cantilever member 109 may be of any suitable stiffness modulus sufficient to allow the instrument 102 to function for its intended purpose. For example, the stiffness modulus may be from about 0.7 $mm^4$ to about 48 $mm^4$, preferably from about 1.0 $mm^4$ to about 4.5 $mm^4$, more preferably about 4.5 $mm^4$.

Figure 1D:
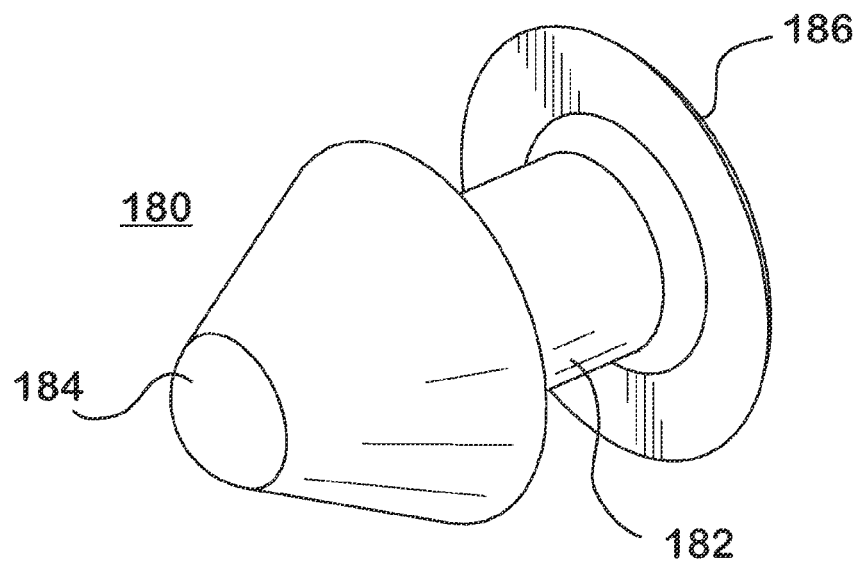
FIG. 1D illustrates a close-up perspective view of an exemplary punctal plug for use with the insertion instrument of FIG. 1B.

The instrument 102 includes cap support portion 111 to support a cap 150, which may be loaded with a punctum plug 180, shown here in close-up of FIG. 1D. The cap support portion 111 has an outer support surface 120 that is generally complementary to the inner surface 160 of the cap 150. The support surface 120 can be provided with a ridge 169B to interlock with a recessed groove 169A formed in the inner surface 160 of the cap 150. The interlock secures the cap 150 to the instrument 102. Preferably, the support surface 120 of the cap support portion 111 is provided with a recessed annular groove 169B to interlock with an annular ridge 169A formed on the inner surface 160 of the cap 150.

With reference to FIGS. 1A and 1B, the cap 150 may have two portions on its outer surface 157. The first portion 162 proximate the first cap end 152 may be generally cylindrical in form. The second portion 164 extends proximate the first portion 162 to a second cap end 156 about and along the longitudinal axis L-L to define a generally tapered surface in the form of a cone. The inner surface 160, which is spaced from the outer surface 157 of the cap 150, may have generally similar configurations as the outer surface 157 to define a hollow cylinder contiguous to a hollow cone about and along the longitudinal axis L-L. The hollow cylinder may have a raised portion proximate the first end 152 of the cap 150 that extends towards the longitudinal axis L-L to preferably define an annular ridge.

As shown in FIG. 1B, the first cap end 152 defines a first opening 154 about the longitudinal axis L-L, and the second cap end 156 defines a second opening 158 about the longitudinal axis L-L. The second opening 158 (FIG. 1D) is configured to be generally the same size or smaller as that of the body 182 of the plug 180 (FIG. 1E) so that the second opening 158, in the form of two half circles or retainer lips 174A and 174B, is able to capture the plug 180 with only the head 184 of the plug 180 protruding from the cap 150.

As shown in FIG. 1C, the second cap end 156 has one or more slits 170 that extend along the longitudinal axis L-L such that the slits 170 provide a diametrical separation, shown here in FIGS. 2B and 2D, between retainer lips 174A and 174B of the second cap end 156. The slits 170 provide first retainer lip 174A and second retainer lip 174B of the second cap end 156 with the ability to flare out in a tulip-like manner during a release of the plug 180.

Figures 3A, 3B:
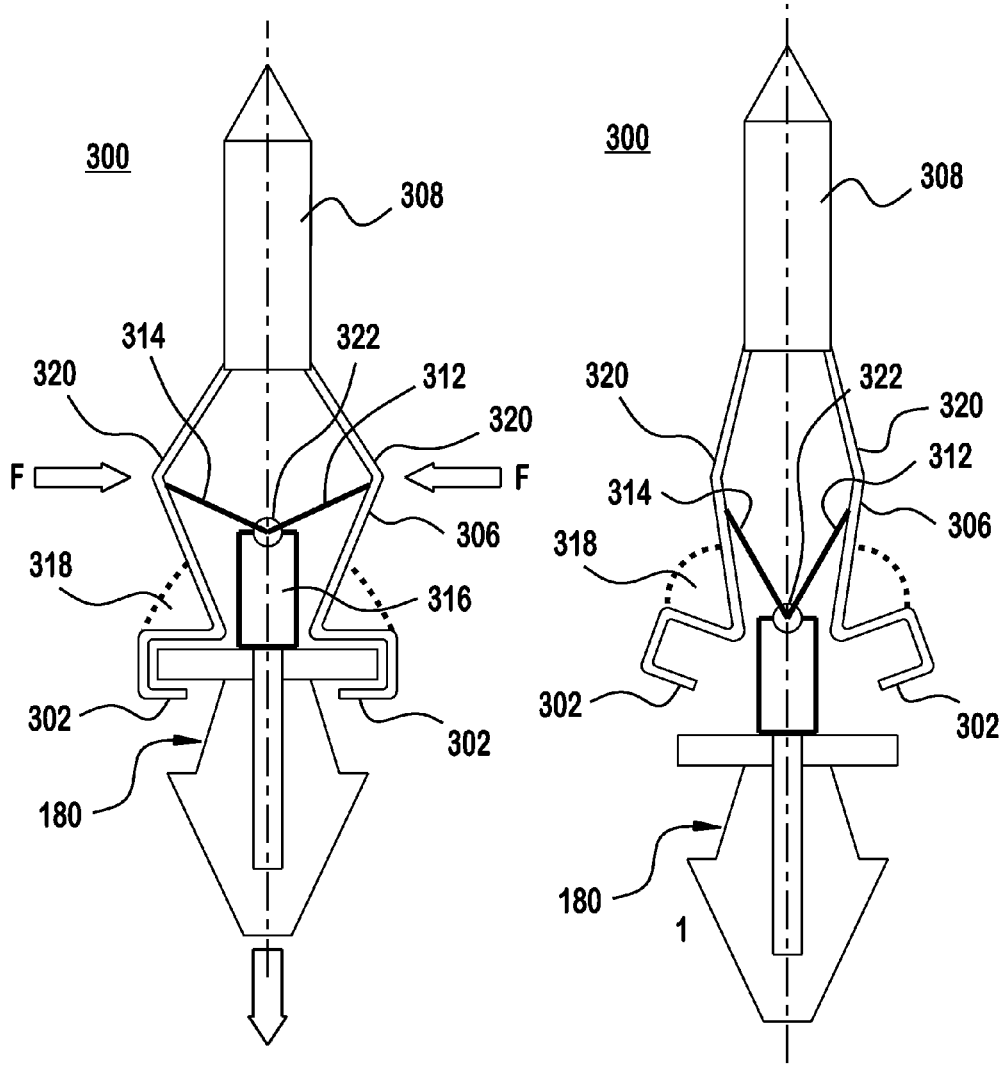
FIGS. 3A and 3B illustrate respective schematic views of another variation of the exemplary system described and illustrated herein.

In an alternative embodiment, shown here in FIG. 3A, the cap 150 is integrated with the instrument 300 and fingers 302 may be added to the retainer lips 174A and 174B second opening to further ensure positive retention of the plug 180 on the cap 150.

The cap 150 will now be described with reference to FIGS. 1B and 1C. In FIG. 1B, the cap 150 can be seen as an elongated body that extends along the longitudinal axis L-L from a proximal or first end 152 to a distal or second end 156. The second end 156 of the cap 150 defines a proximal or first cap opening 154 larger than a distal or second opening 158 defined by the second end 156. The second opening 158 may include at least two slits 170 that extend through a wall 172 of the cap 150 proximate the distal end 107 so that a punctum plug 180 is able to pass through the distal opening 158 upon expansion of the distal opening 158. Preferably, a portion of elongated body has a taper disposed about and along the longitudinal axis L-L to define a generally conic outer surface 157. The inner surface 160 of the elongated body may be spaced apart from the outer surface 157 to define a suitable hollow surface (e.g., cylindrical, conic or combinations thereof).

Preferably, the inner surface 160 defines a generally hollow cone. In the preferred embodiments, the cap 150 has three portions for its outer surface 157: (1) a generally planar tab 151 on (2) a generally cylindrical portion 162, which is integrated with (3) a generally conical portion 164. The inner surface 160 defines the corresponding hollow cylindrical and conic portions. One or more annular rings 169A (raised or recessed) oriented about the longitudinal axis L-L may be provided on the inner surface 160 of the cap 150 so that the ring may interlock with the corresponding annular ring (recessed or raised) 169B on the cap support portion 111. Alternatively, helical rings in the form of screw-on male and female threads may also be provided.

Where the instrument 102 is reusable but the cap 150 and plug 180 are single-use components, several features are provided. A seal 200 can be formed proximate the first cap opening 154 to ensure that whenever the cap 150 is mounted to the instrument 102, there is clear physical indication that the sterility of the cap 150 is no longer assured due to the actuator member 112 piercing the seal 200, which may be hermetic in function. A separate actuator rod 202 can be mounted for engagement with the actuation member 112. The actuator rod 202 may be provided with a slight friction fit to the cap's inner surface 160 proximate the second cap opening 158 with serrated outer surfaces of the rod 202 to ensure that once the actuator rod 202 has been deployed, another plug 180 cannot be installed into the cap 150 due to the action of the serrated surfaces (not shown), which prevents backward movement of the rod 202 towards the proximal end 106.

Referring to FIGS. 2A, 2B, 2C, and 2D, the release of the plug 180 from the cap 150 will now be described. As shown in FIG. 2A, the plug 180 is mounted to the cap 150, which is mounted to the instrument 102 with the actuator 110 in the unreleased or non-actuated position shown in FIG. 1A. In this position, the plug 180 is retained by the lip retainers 174A and 174B (FIG. 2B) of the second opening 158 of the cap 150. To release the plug 180 for its intended use, such as, for example, in the tear duct of a subject, the button 110 (FIG. 1A) is compressed radially towards the longitudinal axis L-L, which causes the actuator member 112 via the hinge 105 to move along the longitudinal axis L-L towards the distal second cap opening 158. Because the actuator member 112 is configured to be larger than the second opening 158, the retainer lips 174A and 174B are forced to move radially outward in a tulip like fashion. As the button 110 is further depressed towards the axis L-L, actuator member 112 continues moving along the longitudinal axis L-L towards the distal end 107 causing actuator 112 to engage against the tail portion of the plug 180. This forces the plug 180 out of the second opening 158. As the actuator member 112 continues moving in the distal direction, the plug 180 will no longer be constrained or retained to the cap 150 and therefore will be released from the cap 150 and into the tear duct.

It is noted that the action of pressing on the actuator 110 may cause the actuator member 112 to translate in a linear direction along the longitudinal axis L-L due to the constraint of the support body opening 114. The linear movement of the actuator member 112 may be simultaneous or in sequence depending on whether there is intentional slop built into the connection between the actuator 110 and the actuator member 112. In the preferred embodiment, both actions (pressing and sliding) are generally simultaneous with some overlaps between the two actions.

In the embodiment of FIGS. 3A and 3B, the retainers 174A and 174B are connected to corresponding cantilevered arms 306 and the cantilevered arms 306 are coupled to a dilation member 108 via angled arms 321. Actuation arms 312 and 314 are connected to the cantilevered arms 306 to ensure that actuation member 316 is forced to move along the longitudinal axis L-L towards the tail portion 182 of the plug 180. Reinforcements 318 are provided between the retainers 174A and 174B and the cantilevered arms 306 to prevent or constrain a flexing of the retainers 174A and 174B relative to the cantilevered arms 306. The cantilevered arms 306 are connected to the angled arms 321 via a connecting hinge 320 for each pair of arms. As in the embodiments of FIGS. 1A and 2A, the connecting hinges 320 may be living hinges.

In a variation of the embodiment of FIG. 3, a double or dual-lever instrument 400 is provided in FIGS. 4A and 4B which may include two cantilevered connecting arms 402 coupled to an actuator body 404. The actuator body 404 is connected to an elongated actuator element 406. Two connecting arm hinges 408 are provided at each end of each cantilevered arm 402. A plug 180 may be mounted on a cap 150. The cap 150 may be mounted to the double lever instrument 400 or integrated as a part of the double lever instrument 400. A dilation member 108 may also be provided in this embodiment to allow a physician to dilate a duct just prior to insertion of the plug 180. In operation, the plug 180 is released by applying forces radially towards the longitudinal axis L-L to compress the actuator 410. This causes each of the cantilevered arms 402 to rotate about its axis while translating along the longitudinal axis L-L, causing the actuator body 404 to force the elongated actuator element 406 to translate along the longitudinal axis L-L. As in the prior embodiments, the cross-section (e.g., circular, conical and the like) of the elongated actuator element 406 may be larger than the opening of the cap 150, which causes the opening 158 of the cap 150 to flare in a tulip-like manner upon entry of the actuator element 406, thereby releasing the plug 180 from the cap.

Another variation, shown in FIGS. 5A and 5B, is provided in which two hinges 506 are utilized for instrument 500. In this instrument 500, the actuator arm 508 is connected to the actuator 504 via a hinge 506. The actuator arm 508 is connected to the actuator member 510 via a pin 322. The actuator member 510 is constrained to translate along the axis L-L due to the opening formed by boss 540. The actuator 504 may also have a hinge 506 for its connection to the dilation member 108. As in the prior embodiments, a cap 550 may also be provided with the plug 180 mounted thereon. Release of the plug 180 in this embodiment is similar to the other embodiments.

It is believed that one of many advantages of the invention over the known system is the ability to switch between different sizes or different configurations of the plugs without the physician straining to find the right plug 180 in order to insert an actuation rod of the known insertion tool. That is, in the known tool, if the plug is not of the right size, the physician would have to either use another tool preloaded with the right size plug or the physician would have to pull the plug out of the known instrument and insert a new plug into an insertion rod of the known tool. In the latter case, the small size of the plug is a significant challenge for the physician to locate and insert the inserter rod of the known tool into the right size plug. In contrast, the embodiments taught herein would allow the physician to simply pull off a wrong-size cap 150 and mount the right size cap 150 without significant visual or physical difficulties in the attachment of the right size plug 180.

Figure 6A:
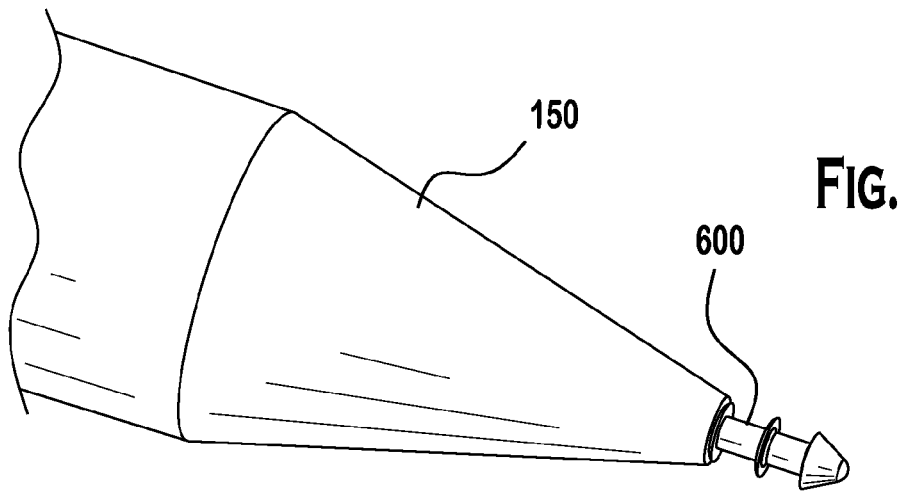
FIGS. 6A-6C are exemplary perspective illustrations of various caps and plugs that can be utilized in the various exemplary instruments described herein to retain a punctum plug.
Figure 6B:
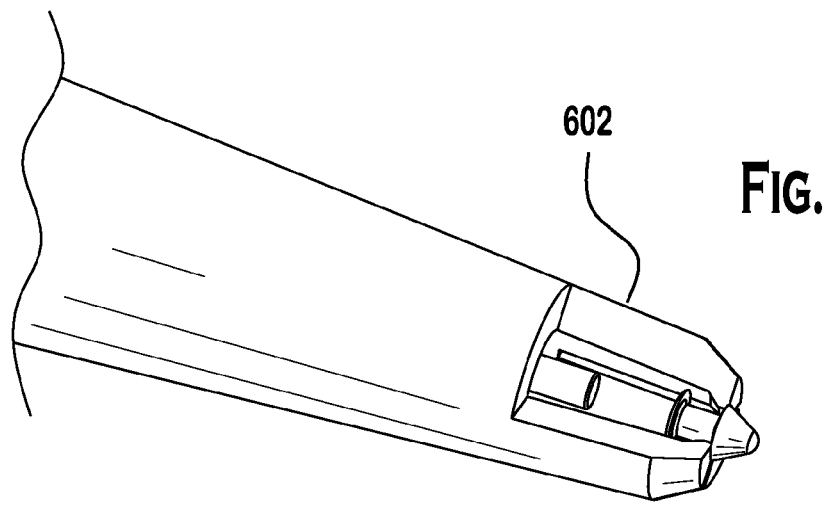
Figure 6C:
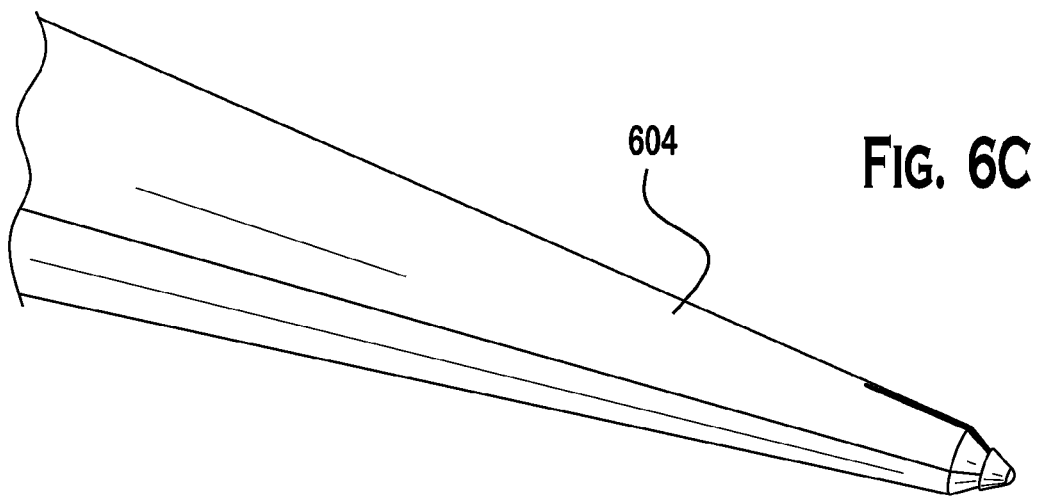

To allow the physicians or health care provider ("HCP") with additional flexibility, the cap 150 and plug 180 may be provided in different configurations, such as, for example, shown in FIGS. 6A, 6B, and 6C. In FIG. 6A, an extended length plug 600 can be utilized with the cap 150. The cap may be in the form of an axially clamped cap 602 (FIG. 6B) or split-seam cap 604 (FIG. 6C).

Figure 7:
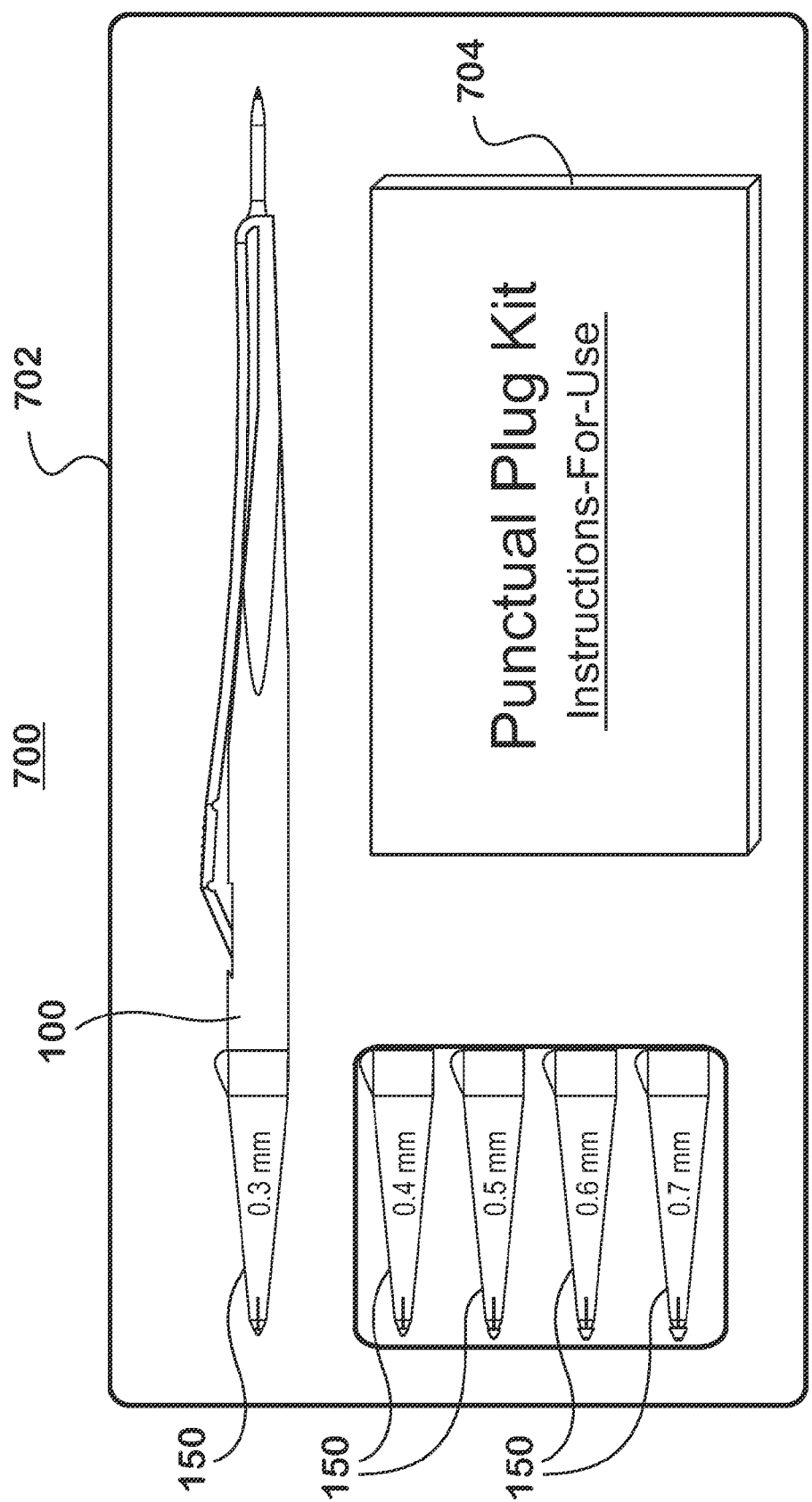
FIG. 7 illustrates an exemplary kit for the various embodiments described herein.

To obtain even greater flexibility for the HCP, a suitable kit in the form such as, for example, FIG. 7 may be provided for the HCP. In this kit 700, an enclosure (e.g., blow-molded case) is provided that contains at least one instrument 102 with a suitable sized plug 180 mounted to the cap 150. Additional caps with different sizes of the plugs (e.g., 0.3 mm, 0.4 mm, 0.5 mm, 0.6 mm, 0.7 mm, 0.8 mm, 0.9 mm and so on with the appropriate size indicia printed on the caps) are provided in the enclosure within a single sterile packaging or within a sub-divided (i.e., multiple individual) sterile packaging. Instructions for use ("IFU") 704 of the kit 700 are provided in the form readable by a person, such as, for example, in the form of a paper medium or electronic medium (e.g., memory stick or CD-ROM). The entire enclosure and its contents can be sterilized using a regulatory approved sterilization technique.

The IFU 704 would include, at a minimum the steps of ensuring that the cap 150 is securely attached to the instrument 102 with the right size plug 180 mounted in the tip of the cap 150; removing the cap 150 if the wrong size plug 180 or wrong tip configuration of the cap 150 is mounted to the instrument 102; securing the right cap 150 and plug 180 configurations to the instrument 102; dilating the tear duct, inserting the plug 180 into the duct and actuating the actuator 110 of the instrument 102 to release or implant the plug 180 into the duct of the subject.

Preferably, the IFU 704 includes the following instructions: (1) Hold the applicator instrument (100) as with a pencil, between the thumb and fingers with the index finger just above the release button (110). At this point, the user should not depress the button. (2) Gently depress the release button (110) until a 'soft-stop' is felt; This is the pre-deployment position. The punctal plug (180) should partially protrude in this position so that the shaft (182) is exposed. (3) Using a gentle, downward, rotational motion, insert the plug until the rim (184) is flush against the punctal opening. Verify that the rim of the plug has not been buried below the punctal ring. If so, gently pull the inserter upward until the rim is sealed properly. (4) With the plug (180) properly positioned, fully depress and hold the release button on the applicator. (5) Remove the applicator while holding the button down. Dispose of the used inserter in a "sharps" container. (6) Using a forceps, gently push down on the collar (186) of the plug (top of the plug) to ensure the plug is completely inserted and the collar is flush with the lid margin.

While preferred embodiments of the present invention have been shown and described herein such embodiments are provided by way of example only. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. An insertion system comprising: an insertion instrument including:
    an insertion instrument including:
    a body extending along a longitudinal axis from a proximal end to a distal end;
    an actuator disposed proximate the distal end, the actuator including an actuation member disposed to move along the longitudinal axis and connected to the actuator with at least one hinge, the actuation member comprising a generally cylindrical rod;
    a cap disposed proximate the distal end of the body, the cap extending from a first cap end to a second cap end along the longitudinal axis, the first cap end defining a first opening about the longitudinal axis and the second cap end defining a second opening about the longitudinal axis, the second cap end further defining at least one slit that extends along the longitudinal axis; and
    a punctum plug having a portion disposed inside the second opening of the cap such that the plug is retained to the cap.

2. The system of claim 1, wherein the proximal end of the body includes a dilation member.

3. The system of claim 1, wherein the actuation member includes an arm disposed at an angle relative to the longitudinal axis and connected to actuator via the at least one hinge.

4. The system of claim 3, wherein the at least one hinge comprises a living hinge.

5. The system of claim 1, wherein the at least one hinge comprises two living hinges.

6. The system of claim 1, wherein the actuator comprises a cantilevered member connected to the dilation member.

7. The system of claim 1, wherein at least a portion of the cap comprises a tapered outer cap surface that surrounds the longitudinal axis to define a generally conical outer surface.

8. The system of claim 7, wherein cap comprises an inner surface spaced apart from the outer cap surface, the inner surface surrounds the longitudinal axis to define a generally hollow cone.

9. The system of claim 8, wherein the inner surface of the cap comprises a raised portion proximate the first end of the cap that extends towards the longitudinal axis.

10. The system of claim 1, wherein the second cap end comprises at least two finger-like retainers separated by the at least one slit.

* * * * *